United States Patent
Emura et al.

(10) Patent No.: US 8,575,086 B2
(45) Date of Patent: Nov. 5, 2013

(54) FLAVOR AND FRAGRANCE COMPOSITIONS

(75) Inventors: Makoto Emura, Kanagawa (JP);
Satoshi Masumura, Kanagawa (JP);
Kenji Maruyama, Kanagawa (JP);
Takeshi Yamamoto, Tokyo (JP)

(73) Assignee: Takasago International Corporation, Tokyo (JP)

(*) Notice: Subject to any disclaimer, the term of this patent is extended or adjusted under 35 U.S.C. 154(b) by 736 days.

(21) Appl. No.: 11/333,367

(22) Filed: Jan. 18, 2006

(65) Prior Publication Data
US 2006/0160719 A1    Jul. 20, 2006

(30) Foreign Application Priority Data
Jan. 18, 2005    (JP) ............................. P.2005-009811

(51) Int. Cl.
*A61K 8/00* (2006.01)
*A61K 8/18* (2006.01)
*A61K 8/02* (2006.01)
*A61Q 13/00* (2006.01)
*A23L 1/28* (2006.01)

(52) U.S. Cl.
USPC ................. 512/1; 426/535; 424/401

(58) Field of Classification Search
USPC ............................................. 512/1
See application file for complete search history.

(56) References Cited

U.S. PATENT DOCUMENTS

| 4,220,561 A | * | 9/1980 | Winter et al. ................. 512/12 |
| 4,224,351 A | | 9/1980 | Sundt et al. ................. 426/535 |
| 5,180,710 A | * | 1/1993 | Naef et al. ................. 512/26 |
| 6,342,644 B1 | | 1/2002 | Sayo et al. ................. 568/830 |

FOREIGN PATENT DOCUMENTS

| JP | 49-24668 | 6/1974 |
| JP | 191940 | 1/2004 |

OTHER PUBLICATIONS

Stereoisomere Aromastoffe Liv. 8-Mercapto-P-Menthan-3-On—Reindarstellung Und Chirospezifische Analyse Der Stereoisomeren; Zeitschrift Für Lebensmittel-Untersuchung Und—Forschung, (1992) 194: 472-376.*

Summary: Köpke et al., "Stereolsomere Aromastoffe", *Z. Lebensm Unters Forsch*, vol. 194 (1992), pp. 372-376.

Kaiser, et al., "Analysis of Buchu Leal Oil", *J. Agric. Food Chem.*, vol. 23, No. 5 (1975), pp. 943-950.

* cited by examiner

*Primary Examiner* — Layla Soroush
(74) *Attorney, Agent, or Firm* — Fitzpatrick, Cella, Harper & Scinto

(57) ABSTRACT

The present invention provides a flavor and fragrance composition which comprises, as the active ingredient, an optically active (1S)-8-mercaptomenthone having an S-form/R-form mixing ratio for the configuration at the 4-position in the range of from 65:35 to 95:5 by weight, wherein the flavor and fragrance composition is for use in food and beverage, fragrances and cosmetics, pharmaceuticals or oral compositions and the like; a product which is scented with the flavor and fragrance composition; and a method for enhancing or modulating odor of the flavor and fragrance composition by adding the optically active (1S)-8-mercaptomenthone.

6 Claims, No Drawings

FLAVOR AND FRAGRANCE COMPOSITIONS

FIELD OF THE INVENTION

The present invention relates to a flavor and fragrance composition which comprises, as an active ingredient, an optically active (1S)-8-mercaptomenthone having an S-form/R-form mixing ratio for the configuration at the 4-position in the range of from 65:35 to 95:5 by weight; and food and beverages, oral compositions, fragrances and cosmetics, pharmaceuticals and the like products scented with the flavor and fragrance composition.

BACKGROUND OF THE INVENTION

In recent years, accompanied by the diversification of various food materials, food additives, foods and beverages (including articles of taste), fragrances and cosmetics, sanitation materials, sundries, pharmaceuticals and the like, new demands for a flavor and fragrance to be used therein have been increasing, and concerns have been directed toward the development of aromatic materials having a highly-tasting unique odor. Particularly, with the recent uprush of the nature-oriented style of people and also from the safety point of view, great concerns have been directed toward the development of new aromatic materials derived from natural compounds, or identical or similar to the natural compounds, with regard to highly tasting fruity flavors and fragrances and tropical flavors and fragrances by which the natural environment can be imaged characteristically.

8-Mercaptomenthone has two chiral centers, and a total of 4 isomers including optical isomers are present. 8-Mercaptomenthone has been found as an essential-oil component of Buchu oil in the past studies, and is synthesized from d-pulegone and l-pulegone whose absolute structures of the natural product are already known. Additionally, according to the angle of rotation thereof, a (1S,4R) isomer has been found as the main component thereof, and a (1S,4S)-isomer as a diastereomer thereof has also been detected simultaneously. However, the mixing ratio thereof has not been disclosed (cf., Non-patent Reference 1).

In addition, synthesis method of each of these 4 isomers has been established and their sensory evaluation has been carried out. As a result, it has been reported that the (1S,4S)-isomer is particularly superior in odor, and the (1S,4R)-isomer also has a desirable odor. On the other hand, it has been reported as an evaluation result that the (1R,4R)-isomer and (1R,4S)-isomer accompany a rubber-like malodor. The products synthesized herein are the natural product having a mixing ratio of the (1S,4S)-isomer and (1S,4R)-isomer of 57:43, and the non-natural product having a mixing ratio of the (1R,4R)-isomer and (1R,4S)-isomer of 58:42 (cf., Non-patent Reference 2).

8-Mercaptomenthone has so far been used as a flavor and fragrance component (cf., Patent Reference 1). However, the 8-mercaptomenthone which has so far been used as the flavor and fragrance is a (1R)-isomer. This is because d-pulegone is used as the starting material which can be obtained easily and inexpensively from the nature. The pulegone used in Reference Example 1 of the Patent Reference 1 is also d-pulegone because its angle of rotation is +220, and the mixing ratio is 3:2. In addition, according to Reference Example 4, 8-mercaptomenthone ($\alpha_D^{20}$=–12.0°) is obtained as a cis-trans mixture using isopulegone ($\alpha_D^{20}$ 124.2°) as the raw material. However, the mixing ratio is unknown.

Patent Reference 1: JP-B-49-24668
Non-patent Reference 1: *J. Agric. Food Chem.*, 23(5), 943-50 (1975)
Non-patent Reference 2: *Z. Lebensm Unters Forsch.*, 194, 372-376 (1992)

SUMMARY OF THE INVENTION

An object of the present invention is to provide a highly-tasting and excellent flavor and fragrance composition which can satisfy the demands for diversifying scented products. Particularly, the invention aims at providing an flavor and fragrance composition which comprises, as the active ingredient, an optically active (1S)-8-mercaptomenthone having an S-form/R-form mixing ratio for the configuration at the 4-position of from 65:35 to 95:5 by weight; and food and beverage, oral compositions, cosmetics, pharmaceuticals and the like products scented with the flavor and fragrance composition.

Under such circumstances, the present inventors have conducted intensive studies and found as a result that an optically active (1S)-8-mercaptomenthone having an S-form/R-form mixing ratio for the configuration at the 4-position of from 65:35 to 95:5 by weight, which is different from the (1R)-8-mercaptomenthone generally used in the market and cannot be easily obtained from natural sources, has a unique odor having a high flavor- and fragrance-creating ability, is excellent in the harmonizing property with other flavors and fragrances to be used, and can impart a deep texture and good body that were insufficient by the conventional analogous compounds derived from natural or processed food and beverage, thereby accomplishing the present invention. Namely, the present invention includes the followings.

(1) A flavor and fragrance composition which comprises, as an active ingredient, an optically active (1S)-8-mercaptomenthone having an S-form/R-form mixing ratio for the configuration at the 4-position in the range of from 65:35 to 95:5 by weight.

(2) The flavor and fragrance composition according to (1), wherein the optically active (1S)-8-mercaptomenthone has a chemical purity of 90% or more and has an optical purity of 90% e.e. or more.

(3) The flavor and fragrance composition according to (1) or (2), which is the flavor.

(4) The flavor and fragrance composition according to (1) or (2), which is the flavor, wherein the optically active (1S)-8-mercaptomenthone is in an amount of from $10^{-5}$ to $10^3$ ppb by weight based on the total weight of the flavor and fragrance composition.

(5) The flavor and fragrance composition according to (1) or (2), which is the fragrance.

(6) The flavor and fragrance composition according to (1) or (2), which is the fragrance, wherein the optically active (1S)-8-mercaptomenthone is in an amount of from $10^{-1}$ to $10^6$ ppb by weight based on the total weight of the flavor and fragrance composition.

(7) A flavored and fragrance-added product comprising the flavor and fragrance composition according to (1) or (2), said product being scented with the flavor and fragrance composition.

(8) The flavored and fragrance-added product according to (7), which is one member selected from the group consisting of food and beverage, oral compositions and pharmaceuticals.

(9) The flavored and fragrance-added product according to (7), which is one member selected from the group consisting of fragrance products, skin-care cosmetics, make-up cosmetics, hair cosmetics, anti-sunburn cosmetics, medicinal cosmetics, hair care products, soap, body lotions, bath liquids, detergents, soft finishing agents, cleaning agents, kitchen detergents, bleaching agents, aerosol agents, deodorant-aromatics, repellents and sundries.

(10) A flavored product which comprises an optically active (1S)-8-mercaptomenthone having an S-form/R-form mixing ratio for the configuration at the 4-position in the range of from 65:35 to 95:5 by weight, in an amount of from $10^{-8}$ to 1 ppb by weight based on the total weight of the flavored product.

(11) A fragrance-added product which comprises an optically active (1S)-8-mercaptomenthone having an S-form/R-form mixing ratio for the configuration at the 4-position in the range of from 65:35 to 95:5 by weight, in an amount of from $10^{-4}$ to $10^5$ ppb by weight based on the total weight of the fragrance-added product.

(12) A method for enhancing or modulating an odor of a flavor and fragrance composition, which comprises adding an optically active (1S)-8-mercaptomenthone having an S-form/R-form mixing ratio for the configuration at the 4-position of from 65:35 to 95:5 by weight, to the flavor and fragrance composition.

(13) The method for enhancing or modulating an odor of a flavor and fragrance composition according to (12), wherein the flavor and fragrance composition is one member selected from the group consisting of synthetic aroma chemicals, natural essential oils, synthetic essential oils, citrus fruit oils and animal aroma chemicals.

By adding the optically active (1S)-8-mercaptomenthone of the present invention having an S-form/R-form mixing ratio for the configuration at the 4-position of from 65:35 to 95:5 by weight, a highly-tasting composition having meaty, green, grape fruits, catty, floral or the like peculiar strong fragrance and flavor can be obtained. This composition is broadly used as perfumes or scented compositions for various food materials, food additives, food and beverage, fragrances and cosmetics, hygiene materials and the like.

DETAILED DESCRIPTION OF THE INVENTION

The following describes the present invention in detail.

The 8-mercaptomenthone is a compound in which the 1-position and 4-position of the cyclohexane moiety are chiral carbon atoms. Illustratively, there are (1S,4R)-8-mercaptomenthone, (1S,4S)-8-mercaptomenthone, (1R,4S)-8-mercaptomenthone and (1R,4R)-8-mercaptomenthone.

The present invention relates to a flavor and fragrance composition which comprises, as an active ingredient, an optically active (1S)-8-mercaptomenthone having an S-form/R-form mixing ratio for the configuration at the 4-position in the range of from 65:35 to 95:5 by weight, preferably in the range of from 70:30 to 90:10 by weight. In this regard, it is preferable that the optically active (1S)-8-mercaptomenthone has a chemical purity of 90% or more, preferably 95% or more and has an optical purity of 90% e.e. or more, preferably 95% e.e. or more.

Each of the aforementioned mixture of R-form and S-form of optically active (1S)-8-mercaptomenthone with a specified ratio shows a strong and fresh passion fruit-like peculiar strong odor. Since the mixture of R-form and S-form of optically active (1S)-8-mercaptomenthone with a specified ratio to be used in the present invention exerts its effect even in an extremely small amount, it can impart the flavor and fragrance to the base materials of various food and beverage and fragrances and cosmetics which require scenting with flavors and fragrances. In this connection, (1R)-8-mercaptomenthone having different configuration at the 1-position is not sufficiently effective, because it accompanies a rubber-like malodor. In addition, even in the case of (1S)-8-mercaptomenthone, a mixture having an S-form/R-form mixing ratio for the configuration oversteping the range of from 65:35 to 95:5 is not sufficiently effective, because it is inferior in terms of the intensity of the odor.

As the mixture of R-form and S-form of optically active (1S)-8-mercaptomenthone with a specified ratio to be used in the present invention, a mixture obtainable by extracting from natural materials can be used, and a mixture obtainable by a chemical synthesis method can also be used. In order to obtain the optically active (1S)-8-mercaptomenthone of the present invention in a large amount, it is desirable to use the mixture obtainable by a chemical synthesis method. The (1S)-8-mercaptomenthone of the present invention is a compound represented by the following formula which is obtainable by adding hydrogen sulfide to an optically active l-pulegone.

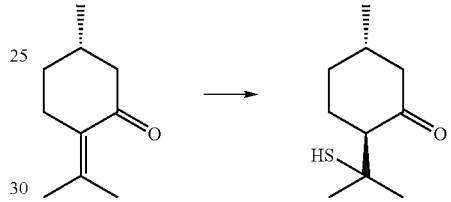

However, since the pulegone which can be found in nature is d-pulegone in almost all cases, a method for synthesizing the optically active l-pulegone in a large amount is required for producing the (1S)-8-mercaptomenthone of the present invention.

The optically active l-pulegone can be obtained, for example, by the reaction represented by the following reaction scheme. In this reaction, l-citronellal (e.g., manufactured by Takasago International Corporation) is used as the starting material, and is firstly converted into d-isopulegol by conducting a cyclization reaction with a Lewis acid. Subsequently, isomerization of the double bond of the thus obtained d-isopulegol is carried out, for example, in the coexistence of a copper-zinc-aluminum catalyst, together with a dehydrogenation reaction to obtain the optically active l-pulegone.

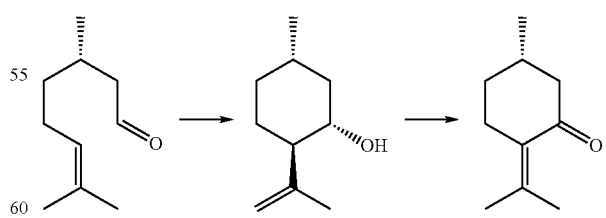

In addition, as is represented by the following reaction scheme, the optically active l-pulegone is also obtainable by carrying out asymmetric hydrogenation of piperitenone (cf., JP-A-2002-30009, herein incorporated by reference).

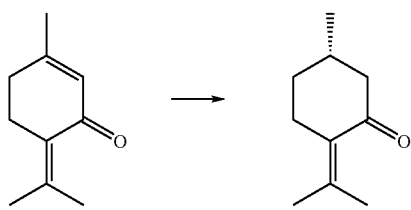

The optically active (1S)-8-mercaptomenthone thus obtained is a mixture of (1S,4R)-8-mercaptomenthone and (1S,4S)-8-mercaptomenthone.

The mixture of R-form and S-form of optically active (1S)-8-mercaptomenthone with a specified ratio according to the present invention is obtainable by applying usual separation purification methods (e.g., column chromatography, distillation and the like) to the (1S)-8-mercaptomenthone obtained in the aforementioned manner. For example, as the method for obtaining an optically active (1S)-8-mercaptomenthone having an S-form/R-form mixing ratio for the configuration at the 4-position of from 65:35 to 95:5 by weight, a chemical purity of 90% or more and an optical purity of 90% e.e. or more, a method in which a fraction secondarily distilled out with the ratio of interest by the distillation is fractionated may be mentioned.

The mixture of (4R)-form and (4S)-form of the optically active (1S)-8-mercaptomenthone according to the present invention shows a strong and fresh passion fruit-like peculiar strong odor. Since the mixture of (4R)-form and (4S)-form of optically active (1S)-8-mercaptomenthone to be used in the present invention exerts its effect even in a small amount, it can impart the fragrance to the base materials of various food and beverage and fragrances and cosmetics which require scenting with flavors and fragrances. In this connection, (1R)-8-mercaptomenthone having different configuration at the 1-position is not sufficiently effective, because it accompanies a rubber-like malodor. In addition, even in the case of (1S)-8-mercaptomenthone, a mixture having an S-form/R-form mixing ratio for the configuration overstepping the range of from 65:35 to 95:5 is not sufficiently effective, because it is inferior in terms of the intensity of the flavor and fragrance.

Also, the mixture of R-form and S-form of optically active (1S)-8-mercaptomenthone of the present invention has a strong and fresh passion fruit-like peculiar strong odor characteristics, and also has significant odor persistency and stability, so that highly-tasting fragrance and flavor compositions can be provided by formulating the mixture. In addition, by formulating the mixture of R-form and S-form of the optically active (1S)-8-mercaptomenthone according to the present invention, the action and effect of flavor and fragrance persistency and flavor and fragrance retention are particularly improved. Namely, the odor of flavor and fragrance composition may be enhanced or modulated by adding the optically active (1S)-8-mercaptomenthone having an 3-form/R-form mixing ratio for the configuration at the 4-position of from 65:35 to 95:5 by weight.

The optically active (1S)-8-mercaptomenthone has an S-form/R-form mixing ratio for the configuration at the 4-position in the range of from 65:35 to 95:5 by weight, preferably in the range of from 70:30 to 90:10 by weight. In this regard, it is preferable that the optically active (1S)-8-mercaptomenthone has a chemical purity of 90% or more, preferably 95% or more and has an optical purity of 90% e.e. or more, preferably 95% e.e. or more.

Flavor and fragrance compositions prepared by further adding a generally used flavor and fragrance component to the mixture of R-form and S-form of the optically active (1S)-8-mercaptomenthone according to the invention can also be used as a fragrance component and a flavor component. As the additional flavors and fragrances which is added and used, various synthetic aroma chemicals, natural aroma chemicals, natural essential oils, citrus fruit oils, animal aroma chemicals and the like can be mentioned, and a floral green-like flavor and fragrance composition is particularly desirable. For example, a broad range of fragrance components described in 'Arctander S., "Perfume and Flavor Chemicals", published by the author, Montclair, N.J. (U.S.A.) in 1969' can be used. Their typical examples include α-pinene, limonene, cis-3-hexenol, phenylethyl alcohol, styralyl acetate, eugenol, rose oxide, linalool, benzaldehyde, muscone, Thesaron (manufactured by Takasago International Corporation) and the like.

Illustratively, when the mixture of (4R)-form and (4S)-form of the optically active (1S)-8-mercaptomenthone according to the invention is added, for example, to bergamot oil, galbanum oil, lemon oil, geranium oil, lavender oil, mandarin oil or the like natural essential oil, a novel flavor and fragrance composition with emphasized persistency, in which the fragrance and flavor originally possessed by the natural essential oil are improved in terms of mildness, richness, freshness and high tasting, and diffusivity and holding ability thereof are enhanced, can be prepared.

In addition, when the mixture is added to, for example, a strawberry, lemon, orange, grapefruit, apple, pineapple, banana, melon, green tea, Oolong tea, black tea or the like flavor composition, which is prepared from various synthetic aroma chemicals, natural aroma chemicals, natural essential oils, citrus fruit oils, tea extracts, animal aroma chemicals and the like, a flavor and fragrance composition with emphasized persistency, which is provided with mild, rich and natural-like fruity or tropical flavor and fragrance and is further provided with a fresh and high-tasting fragrance and in which the diffusivity and holding ability are improved, can be prepared.

The amount of the mixture of (4R)-form and (4S)-form of the optically active (1S)-8-mercaptomenthone according to the present invention to be added to the flavor and fragrance composition varies depending on the kind and purpose of the flavors and fragrances. For example, in the case of fragrance compositions, the amount of the mixture is preferably from $10^{-1}$ to $10^6$ ppb by weight based on the total weight of the composition. In addition, in the case of flavor compositions, the amount of the mixture is preferably from $10^{-5}$ to $10^3$ ppb by weight based on the total weight of the composition.

In addition, it may be blended with one or two or more generally-used flavor- and flagrance-retaining agents, and for example, it is possible to use the mixture together with ethylene glycol, propylene glycol, dipropylene glycol, glycerol, hexylene glycol, benzyl benzoate, triethyl citrate, diethyl phthalate, Hercolyn, middle-chain fatty acid triglyceride and the like.

According to the present invention, fragrance-added products and flavored products can be provided by blending the optically active (1S)-8-mercaptomenthone alone, or an fragrance composition or a flavor composition containing the compound, in such an appropriate amount that the unique fragrance and flavor thereof can be added, for example with fragrance products, skin-care cosmetics, make-up cosmetics, hair cosmetics, anti-sunburn cosmetics, medicinal cosmetics, hair-care products, soap, body lotions, bath liquids, detergents, soft finishing agents, cleaners, kitchen detergents, bleaching agents, aerosol agents, deodorant-aromatics, repellents and sundries; or with food and beverage, oral compositions and pharmaceuticals.

For example, there may be mentioned perfumed water, Eau de Perfum, Eau de toilette, Eau de cologne and the like as the fragrance products; and face washing cream, vanishing cream, cleansing cream, cold cream, massage cream, milky lotion, toilette lotion, beauty wash, pack, make remover and the like as the skin-care cosmetics; foundation, face powder, pressed powder, talcum powder, rouge, lipstick, lip cream, cheek rouge, eye liner, mascara, eye shadow, eyebrow-color, eye pack, nail enamel, enamel remover and the like as the make-up cosmetics; pomade, brilliantine, set lotion, hair stick, hair solid, hair oil, hair treatment, hair cream, hair tonic, hair liquid, hair spray, bandlin, hair growth agent, hair dye and the like as the hair cosmetics; suntan product, sun screen product and the like as the anti-sunburn cosmetics; and antiperspirant, after-shaving lotion and gel, permanent wave agent, medicinal soap, medicinal shampoo, medicinal skin cosmetics and the like as the medicinal cosmetics.

There may be mentioned shampoo, rinse, rinse-in-shampoo, conditioner, treatment, hair pack and the like as the hair-care products; and toilet soap, bath soap, scented soap, transparent soap, synthetic soap and the like as the soap; body soap, body shampoo, hand soap and the like as the body lotions; and bath agents (bath salt, bath tablet, bath liquid or the like), foam bath (bubble bath or the like), bath oil (bath perfume, bath capsule or the like), milk bath, bath jerry, bath cube and the like as the bath liquids.

Further, there may be mentioned heavy detergent for clothing, light detergent for clothing, liquid detergent, laundry soap, compact detergent, powder soap and the like as the detergents; and softener, furniture care and the like as the soft finishing agents; cleanser, house cleaner, toilet cleaner, bath cleaner, glass cleaner, mold remover, waste pipe cleaner and the like as the cleaners; kitchen soap, kitchen synthetic soap, tableware detergents and the like as the kitchen detergents; oxidation type bleaching agent (e.g., a chlorine base bleaching agent or oxygen base bleaching agent), reduction type breaching agent (e.g., sulfur base bleaching agent), optical bleaching agent and the like as the bleaching agents; spray-type aerosols, powder spray and the like as the aerosol agents; deodorants or deodorizers of solid-type, gel-type, liquid-type and the like as the deodorant-aromatics; and tissue paper, toilette paper and the like as the sundries.

Moreover, there may be mentioned fruit juice beverages, fruit wines, milk beverages, carbonated beverages, soft beverages, drinking agents and the like beverages; and ice creams, sherbets, ice candies and the like frozen desserts; Japanese-style and Western-style confectioneries; jams; candies; jellies; gums; breads; coffees, cocoas, black teas, oolong teas, green teas and the like luxury beverages; Japanese-style soup, Western-style soup, Chinese-style soup and the like soups; flavor and condiment; various types of instant beverages and foods; various types of snack foods and the like as the foods and beverages. As the oral compositions, dentifrice, oral washing agent, mouse wash, troche, chewing gums and the like may be mentioned. Further, as the pharmaceuticals, skin external preparations such as cataplasmas and ointments; internal medicines and the like may be mentioned.

When the optically active (1S)-8-mercaptomenthone of the present invention is used in fragrance products, basic skin cares, finishing cosmetics, hair cosmetics, anti-sunburn cosmetics, medicinal cosmetics, hair-care products, soap, body lotions, bath liquids, detergents, soft finishing agents, cleaning agents, kitchen detergents, bleaching agents, aerosol agents, deodorant-aromatics, repellents and sundries; or in food and beverage, oral compositions, pharmaceuticals and the like, the compound may be used directly, or by selecting optional shapes in accordance with the respective purposes, such as a liquid state in which the compound is dissolved in alcohols, propylene glycol, glycerol and the like polyhydric alcohols; a state in which the compound is mixed with gum arabic, tragacanth gum and the like natural gummy matters; an emulsified state in which the compound is emulsified with glycerol fatty acid ester, sucrose fatty acid ester and the like emulsifiers; a powdery state in which the compound is coated using natural gummy matters such as gum arabic, gelatin, dextrin and the like fillers; a solubilized or dispersed state in which the compound is solubilized or dispersed using surfactants such as a nonionic surfactant, an anionic surfactant, a cationic surfactant, an ampholytic surfactant and the like; a microcapsular state which is obtainable by treating the compound with a capsulation agent; and the like.

In addition, it is possible to use the aforementioned flavor and fragrance compositions in a stable and releasable state by including the compositions in an inclusion agent such as cyclodextrin These are used by optionally selecting those which are suited for the shapes of the final product, such as a liquid state, a solid state, a powder state, a gel state, a mist state, an aerosol state and the like.

In this connection, amount of the (1S)-8-mercaptomenthone of the invention to be added to the fragrance-added products such as fragrance products, skin-care cosmetics, make-up cosmetics, hair cosmetics, anti-sunburn cosmetics, medicinal cosmetics, hair care products, soap, body lotions, bath liquids, detergents, soft finishing agents, cleaning agents, kitchen detergents, bleaching agents, aerosol agents, deodorant-aromatics, repellents and sundries is optionally controlled in response to the expected effects and actions of respective cases and is generally approximately from $10^{-4}$ to $10^5$ ppb by weight based on the total weight of the fragrance-added product.

Also, amount of the (1S)-8-mercaptomenthone of the invention to be added to flavored products such as food and beverage, oral compositions and pharmaceuticals is optionally controlled in response to the expected effects and actions of respective cases and is generally approximately from $10^{-8}$ to 1 ppb by weight based on the total weight of the flavored product.

EXAMPLES

The present invention will be explained below in more detail by reference to Examples and Comparative Examples, but the present invention should not be construed as being limited to the following Examples, and it is possible to change them within such a range that they do not overstep the scope of the present invention.

In this connection, in the formulations described below, the % means weight %, and the part means part by weight unless otherwise noted.

The analyses in the examples were carried out using the following instruments for analysis.

<Angle of Rotation>
Instrument; DIP-370 (mfd. by Japan Spectroscopic Co., Ltd.)
<Proton Nuclear Magnetic Resonance Spectrum ($^1$H-NMR)>
Instrument: AM-400 type (400 MHz) (mfd. by Bruker Bio-Spin GmbH)
Internal Standard Substance: tetramethylsilane
<Infrared Absorption Spectrum IR)>
Instrument: Nicolet Avatar 360 FT-IR (mfd. by Nicolet Japan)

<Mass Spectrum (MS)>
Instrument; M-80B mass spectrometer (ionization voltage: 20 eV) (mfd. by Hitachi, Ltd.)
<Gas Chromatograph>
Instrument: HP-5890 (mfd. by Hewlett Packard)
Column: PEG BC-WAX (0.25 mm×50 m) (mfd. by GL Sciences Inc.)

Synthesis Example 1

Synthesis of l-pulegone from l-citronellal (1) Synthesis of d-isopulegol

In a stream of argon, 1.44 g of zinc bromide was added to a 300 ml capacity reaction vessel, 100 g of l-citronellal and 50 ml of toluene were subsequently added thereto, and then they were stirred at 110° C. for 17 hours. After completion of the reaction, 50 ml of 4% sodium hydroxide aqueous solution was added thereto, separation was carried out, toluene was evaporated, and the distillation was subsequently carried out to obtain 71 g of d-isopulegol as a colorless oily substance.

(2) Synthesis of l-pulegone

A 50 g portion of the d-isopulegol obtained in (1) was stirred at 150° C. for 8 hours in the coexistence of 200 mg of a copper-zinc-aluminum catalyst to carry out isomerization of the double bond together with dehydrogenation reaction, thereby obtaining 40 g of l-pulegone (yield 81%).

Synthesis Example 2

Synthesis of l-pulegone from piperitenone

A 500 ml capacity autoclave was charged with 150 g (1 mol) of piperitenone, 18.6 mg (0.04 mmol) of bis(1,5-cyclooctadiene)rhodium (I) hexafluorophosphate (to be referred to as [Rh(cod)$_2$]PF$_6$ hereinafter), 47.2 mg (0.04 mmol) of (R)-(4,4'-bi-1,3-benzodioxiol)-5,5'-diylbis(di(3,5-di-tert-butyl-4-methoxyphenyl)phosphine (to be referred to as (R)-DTBM-SEGPHOS hereinafter), 14.8 mg (0.02 mmol) of tetramethylenebis(triphenylphosphonium bromide) (to be referred to as BrPPh$_3$(CH$_2$)$_4$PPh$_3$Br hereinafter) and 7.5 ml of ethyl acetate, and the reaction was carried out at 50° C. for 20 hours under a hydrogen pressure of 3 MPa. After completion of the reaction, hydrogen was purged, and the reaction solution was concentrated and distilled under a reduced pressure to obtain 136.8 g of l-pulegone (yield 90%).

Synthesis Example 3

Synthesis of (1S)-mercaptomenthone from l-pulegone

A reactor equipped with a thermometer and a gas-introducing tube was charged with the l-pulegone (3 g, 23 mmol) obtained in Synthesis Example 1 or Synthesis Example 2 and methylene chloride (30 ml), anhydrous aluminum chloride (612 mg, 0.2 equivalent) was added thereto, and then hydrogen sulfide gas was blown through the gas-introducing tube for 3 hours. After completion of the reaction, a portion of the reaction mixture was taken out, and the conversion ratio was measured by a gas chromatography to find that it was 100%.

After releasing the remaining hydrogen sulfide from the reaction mixture by nitrogen, a crude product was obtained in the usual way by dilute hydrochloric acid treatment, washing with water and concentration.

By distilling the thus obtained crude product under a reduced pressure (95° C./600 Pa), 2.8 g (yield 65%) of the title compound was obtained with a purity of 96%.

Ratio of S-form to R-form for the configuration at the 4-position of this compound was 60:40. A 1.0 g portion of the thus obtained (1S)-8-mercaptomenthone having an S-form/R-form ratio for the configuration at the 4-position of 60:40 was purified by a recycling method using a gas chromatographic separation.

(1S,4R)-8-Mercaptomenthone (cis-form)

$[\alpha]_D^{20}$ −43 5° (c=1.3, CH$_3$OH)
MS (m/z): 153 (—SH)
IR (neat): 1709, 2583 cm$^{-1}$
$^1$H-NMR (CDCl$_3$, δppm): 1.02 (3H, d), 1.40 (6H, s), 2.30 (1H, s)

(1S,4S)-8-Mercaptomenthone (trans-form)

$[\alpha]_D^{20}$ +29.6° (c=1.5, CH$_3$OH)
MS (m/z): 153 (—SH)
IR (neat); 1709, 2583 cm$^{-1}$
$^1$H-NMR (CDCl$_3$, δ ppm): 0.96 (3H, d), 1.40 (3H, s), 1.45 (3H, s), 2.35 (1H, s)

Synthesis Example 4

Preparation of S-form/R-form mixture for the configuration at the 4-position of (1S)-8-mercaptomenthone The fore-running and aft-running of 2.8 g of the (1S)-8-mercaptomenthone wherein S-form/R-form for the configuration at the 4-position was 60:40, obtained in Synthesis Example 3, were cut off under a reduced pressure, and the main fraction was cracked under a condition with a boiling point of 90° C. at 200 Pa to obtain 2.0 g of (1S)-8-mercaptomenthone wherein S-form/R-form for the configuration at the 4-position was 75/25.

Synthesis Example 5

Synthesis of d-pulegone from d-citronellal (1) Synthesis of l-isopulegol

In a stream of argon, 1.44 g of zinc bromide was added to a 300 ml capacity reaction vessel, 100 g of d-citronellal and 50 ml of toluene were subsequently added thereto, and then they were stirred at 110° C. for 17 hours. After completion of the reaction, 50 ml of 4% sodium hydroxide aqueous solution was added thereto, the layers were separated, toluene was evaporated, and the distillation was carried out to obtain 71 g of l-isopulegol as a colorless oily substance.

(2) Synthesis of d-pulegone

A 50 g portion of the l-isopulegol obtained in (1) was stirred at 150° C. for 8 hours in the coexistence of 200 mg of a copper-zinc-aluminum catalyst to carry out isomerization of the double bond together with dehydrogenation reaction, thereby obtaining 43 g of d-pulegone (yield 87%).

Synthesis Example 6

Synthesis of d-pulegone from piperitenone

A 500 ml capacity autoclave was charged with 150 g (1 mol) of piperitenone, 18.6 mg (0.04 mmol) of [Rh(cod)$_2$]PF$_6$, 47.2 mg (0.04 mmol) of (S)-DIBM-SEGPHOS, 14.8 mg (0.02 mmol) of $BrPPh_3(CH_2)_4PPh_3Br$ and 7.5 ml of ethyl acetate, and the reaction was carried out at 50° C. for 20 hours under a hydrogen pressure of 3 MPa. After completion of the reaction, hydrogen was purged, and the reaction solution was concentrated and distilled under a reduced pressure to obtain 136.8 g of d-pulegone (yield 90%).

Synthesis Example 7

Synthesis of (1R)-mercaptomenthone from d-pulegone

A reactor equipped with a thermometer and a gas-introducing tube was charged with the d-pulegone (3 g, 23 mmol) obtained in Synthesis Example 5 and methylene chloride (30 ml), anhydrous aluminum chloride (612 mg, 0.2 equivalent) was added thereto, and then hydrogen sulfide gas was blown through the gas-introducing tube for 3 hours. After completion of the reaction, a portion of the reaction mixture was taken out, and the conversion ratio was measured by a gas chromatography to find that it was 100%.

After releasing the remaining hydrogen sulfide from the reaction mixture by nitrogen, a crude product was obtained in the usual way by dilute hydrochloric acid treatment, washing with water and concentration.

By distilling the thus obtained crude product under a reduced pressure (95° C./600 Pa), 3 g (yield 70%) of the title compound was obtained with a purity of 96%.

Ratio of trans-form to cis-form of the compound was 60:40. A 1.0 g portion of the thus obtained (1R)-8-mercaptomenthone wherein trans-form/cis-form was 60/40 was purified by a recycling method using a gas chromatographic separation.

(1R,4S)-8-Mercaptomenthone (cis-form)

$[\alpha]_D^{20}$ +43.3° (c=1.1, $CH_3OH$)
MS (m/z): 153 (—SH)
IR (neat): 1709, 2583 $cm^{-1}$
$^1$H-NMR ($CDCl_3$, δ ppm): 1.02 (3H, d), 1.40 (6H, s), 2.30 (1H, s)

(1R,4R)-8-Mercaptomenthone (trans-form)

$[\alpha]_D^{20}$ −29.7° (c=1.2, $CH_3OH$)
MS (m/z): 153 (—SH)
IR (neat): 1709, 2583 $cm^{-1}$
$^1$H-NMR ($CDCl_3$, δ ppm): 0.96 (3H, d), 1.40 (3H, s), 1.45 (3H, s), 2.35 (1H, s)

Synthesis Example 8

Preparation of R-form/S-form mixture for the configuration at the 4-position of (1R)-8-mercaptomenthone The fore-running and aft-running of 2.8 g of the (1R)-8-mercaptomenthone wherein R-form/S-form for the configuration at the 4-position was 60/40, obtained in Synthesis Example 7, were cut off under a reduced pressure, and the main fraction was cracked under a condition with a boiling point of 90° C. at 200 Pa to obtain 2.0 g of (1R)-8-mercaptomenthone wherein R-form/S-form for the configuration at the 4-position was 75/25.

Inventive Example 1

<Evaluation of Odor Quality>

Regarding the 8-mercaptomenthone obtained in each of the aforementioned Synthesis Examples, respective samples were put on bottle mouths and filter papers to carry out the sensory evaluation by 7 perfumers having an experience in this field of 5 years or more. The evaluation results are shown in Table 1.

TABLE 1

| Compound name | Odor quality |
| --- | --- |
| (1S)-Mercaptomenthone of 75:25 obtained in Synthesis Example 4 | A clean and fresh odor which reminds the perfumers of the strong and fresh sarcocarp and seed of passion fruit |
| (1S)-Mercaptomenthone of 60:40 obtained in Synthesis Example 3 | Has a passion fruit-like odor but is lack in strength and accompanies miscellaneous impressions |
| (1S,4R)-Mercaptomenthone obtained in Synthesis Example 3 | An odor which reminds the perfumers of Buchu oil |
| (1S,4S)-Mercaptomenthone obtained in Synthesis Example 3 | A natural passion fruit-like odor which is excellent in terms of impact and has a clean and fresh image |
| (1R)-Mercaptomenthone of 75:25 obtained in Synthesis Example 8 | A strong and fruity odor, but it accompanies a rubbery malodor |
| (1R)-Mercaptomenthone of 60:40 obtained in Synthesis Example 7 | A strong but rubbery malodor, which is not desirable as food |
| (1R,4S)-Mercaptomenthone obtained in Synthesis Example 7 | An unpleasant malodor having a rubber-like malodor |
| (1R,4R)-Mercaptomenthone obtained in Synthesis Example 7 | A crude malodor which reminds the perfumers of the un-fresh onion |
| Buchu oil-isolated natural mercaptomenthone | A natural odor but is lack in strength and has somewhat miscellaneous impressions |

As shown above, the compound of the present invention, from which the rubbery miscellaneous malodor as a weak point of (1R)-mercaptomenthone was excluded and which has both of the desirable characteristics of (1S,4R)- and (1S,4S)-mercaptomenthone, reminded the strong and fresh passion fruit and possessed a clean, fresh and highly-tasting strong characteristic odor.

Inventive Example 2

A 1 ppb ethanol solution of the (1S)-8-mercaptomenthone obtained in Synthesis Example 4, wherein the mixing ratio of S-form/R-form for the configuration at the 4-position was 75:25, was added at a ratio of 0.1 part to 100 parts of a green tea extract obtained by pouring 300 ml of hot water of 90° C. to 10 g of green tea leaves and then filtering the tea leaves after allowing to stand for about 1 minute, thereby obtaining the green tea beverage of the present invention which contains 0.001 ppb of said (1S)-8-mercaptomenthone. This product possessed a soft and mellow green odor characteristic to a fresh tea, with reduced bitter taste and rough taste.

Inventive Example 3

(1) A green tea extract obtained by pouring 30 liters of hot water of 90° C. to 1 kg of green tea leaves and then filtering the tea leaves after allowing to stand for about 1 minute was concentrated 100 times to prepare a flavor composition for green tea beverage use.

(2) A 10 ppb ethanol solution of the (1S)-8-mercaptomenthone obtained in Synthesis Example 4, wherein the mixing ratio of S-form/R-form for the configuration at the 4-position was 75:25, was added at a ratio of 0.002 part to 100 parts of the flavor composition for green tea use obtained in the above (1), thereby obtaining the flavor composition for green tea beverage use of the present invention which contains 0.0002 ppb of said (1S)-8-mercaptomenthone.

(3) The flavor composition obtained in the above (2) was added at a ratio of 1 part to 100 parts of a green tea extract obtained by pouring 300 ml of hot water of 90° C. to 10 g of green tea leaves and then filtering the tea leaves after allowing to stand for about 1 minute, thereby producing a green tea beverage which contains (1S)-8-mercaptomenthone wherein the mixing ratio of S-form/R-form for the configuration at the 4-position was 75:25 [concentration of (1S)-8-mercaptomenthone: about 0.000002 ppb]. The green tea beverage thus obtained was a green tea beverage having a soft and mellow green odor characteristic to a fresh tea, with reduced bitter taste and rough taste, and the good odor was not lost but maintained even after a lapse of 24 hours.

Inventive Examples 4 and 5, Comparative Examples 1 and 2

(1) The flavor composition of Inventive Example 4 containing (1S)-8-mercaptomenthone in a concentration of 0.10 ppb was prepared by adding the (1S)-8-mercaptomenthone obtained in Synthesis Example 4, wherein the mixing ratio of S-form/R-form for the configuration at the 4-position was 75:25, to the flavor composition for green tea beverage use shown in the following Table 2.

In addition, a product prepared by not adding the aforementioned (1S)-8-mercaptomenthone was used as Comparative Example 1.

TABLE 2

| Components | Inventive Example 4 | Comparative Example 1 |
| --- | --- | --- |
| Cis-jasmone | 0.02 | 0.02 |
| Cis-3-hexenol | 0.15 | 0.15 |
| Trans-3-hexenal | 0.1 | 0.1 |
| Jasmine lactone | 0.001 | 0.001 |
| β-Ionone | 0.005 | 0.005 |
| Indole | 0.01 | 0.01 |
| Hexanoic acid | 0.1 | 0.1 |
| (1S)-8-Mercaptomenthone | 0.000001 | — |
| Purified water | 40.0 | 40.0 |
| Ethanol | balance | balance |
| Total | 100.0 | 100.0 |

(2) Each of the flavor compositions obtained in the above (1) (the flavor compositions of Inventive Example 4 and Comparative Example 1) was added at a ratio of 1 part to 100 parts of a green tea extract obtained by pouring 300 ml of hot water of 90° C. to 10 g of green tea leaves and then filtering the tea leaves after allowing to stand for about 1 minute, thereby producing a green tea beverage which contains 0.001 ppb in concentration of (1S)-8-mercaptomenthone wherein the mixing ratio of S-form/R-form for the configuration at the 4-position was 75:25 (Inventive Example 5) and another green tea beverage to which (1S)-8-mercaptomenthone was not added (Comparative Example 2).

(3) Sensory comparison evaluation of both of the green tea beverages obtained in the above (2) was carried out by a panel of 7 specialists. As a result, all members of the panel judged that a green tea-specific deep body, which was not present in the beverage of Comparative Example 2, was added to the beverage of Inventive Example 5 produced by adding the compound.

Inventive Example 6

A 10 ppb ethanol solution of the (1S)-8-mercaptomenthone obtained in Synthesis Example 4, wherein the mixing ratio of S-form/R-form for the configuration at the 4-position was 75:25, was added in an amount of 0.002 part to 100 parts of an oolong tea extract obtained by pouring 300 ml of hot water of 100° C. to 10 g of oolong tea leaves and then filtering the tea leaves after allowing to stand for about 3 minutes, thereby obtaining the oolong tea beverage of the present invention which contains 0.0002 ppb of the (1S)-8-mercaptomenthone. This product possessed a fragrance which has a deep oolong tea-like image and accompanies a ripen feeling.

Inventive Example 7

(1) An oolong tea extract obtained by pouring 30 liters of hot water of 100° C. to 1 kg of oolong tea leaves and then filtering the tea leaves after allowing to stand for about 3 minutes was concentrated 100 times to prepare an flavor composition for oolong tea beverage use.

(2) A 10 ppb ethanol solution of the (1S)-8-mercaptomenthone obtained in Synthesis Example 4, wherein the mixing ratio of S-form/R-form for the configuration at the 4-position was 75:25, was added at a ratio of 0.002 part to 100 parts of the flavor composition obtained in the above (1), thereby obtaining the aroma composition for oolong tea beverage use of the invention which contains 0.0002 ppb of said (1S)-8-mercaptomenthone.

(3) The flavor composition obtained in the above (2) was added at a ratio of 1 part to 100 parts of an oolong tea extract obtained by pouring 300 ml of hot water of 100° C. to 10 g of oolong tea leaves and then filtering the tea leaves after allowing to stand for about 3 minutes, thereby producing an oolong tea beverage which contains about 0.000002 ppb in concentration of (1S)-8-mercaptomenthone wherein the mixing ratio of S-form/R-form for the configuration at the 4-position was 75:25. This oolong tea beverage was possessed of an odor which has a deep oolong tea-like image and accompanies a ripen feeling, and the good odor was not lost but maintained even after a lapse of 24 hours.

Inventive Example 8, Comparative Example 3

(1) By adding the (1S)-8-mercaptomenthone obtained in Synthesis Example 4, wherein the mixing ratio of S-form/R-form for the configuration at the 4-position was 75:25, to the flavor composition for oolong tea beverage use shown in the following Table 3, the flavor composition of Inventive Example 8 containing the (1S)-8-mercaptomenthone in a concentration of 0.10 ppb was prepared. In addition, a product prepared by not adding the (1S)-8-mercaptomenthone was used as Comparative Example 3.

TABLE 3

| Components | Inventive Example 8 | Comparative Example 3 |
|---|---|---|
| Cis-3-Hexenol | 0.001 | 0.001 |
| Eugenol | 0.002 | 0.002 |
| Geraniol | 0.002 | 0.002 |
| δ-Decalactone | 0.002 | 0.002 |
| Linalool | 0.004 | 0.004 |
| Methyl jasmonate | 0.01 | 0.01 |
| Phenylethyl acetate | 0.02 | 0.02 |
| Phenylethyl alcohol | 0.04 | 0.04 |
| Jasmine lactone | 0.2 | 0.2 |
| (1S)-8-Mercaptomenthone | 0.000001 | — |
| Water | 40.0 | 40.0 |
| Ethanol | balance | balance |
| Total | 100.0 | 100.0 |

(2) Each of the flavor compositions obtained in the above (1) (the flavor compositions of Inventive Example 8 and Comparative Example 3) was added at a ratio of 0.1 part to 100 parts of an oolong tea extract obtained by pouring 300 ml of hot water of 100° C. to 10 g of oolong tea leaves and then filtering the tea leaves after allowing to stand for about 3 minutes, thereby producing an oolong tea beverage which contains 1 ppb in concentration of (1S)-8-mercaptomenthone wherein the mixing ratio of S-form/R-form for the configuration at the 4-position was 75:25 (Inventive Example 9) and another oolong tea beverage to which (1S)-8-mercaptomenthone was not added (Comparative Example 4).

(3) Sensory comparison evaluation of the oolong tea beverages obtained in the above (2) was carried out by a panel of 7 specialists. As a result, all members of the panel pointed out that an oolong tea-specific deep body, which was not present in the beverage of Comparative Example 4, was added to the aforementioned beverage of Inventive Example 5 produced by adding (1S)-8-mercaptomenthone.

Inventive Example 10

(1) In this Inventive Example 10, a powdered tea pudding to which (1S)-8-mercaptomenthone wherein the mixing ratio of S-form/R-form for the configuration at the 4-position was 75:25 was added and contained therein was produced using a formulation for powdered tea pudding use shown in the following Table 4.

TABLE 4

| Components | Part(s) by weight |
|---|---|
| Sucrose | 8.0 |
| Whip cream (vegetable fat content: 40%) | 10.0 |
| Whole milk condensed whole milk, sweetened | 6.0 |
| Skim milk powder | 5.0 |
| Powdered tea | 0.5 |
| Gelling agent | 0.45 |
| Emulsifying agent | 0.1 |
| Coloring agent | 0.05 |
| Powdered tea (Matcha) flavor | 0.1 |

TABLE 4-continued

| Components | Part(s) by weight |
|---|---|
| (1S)-8-Mercaptomenthone 10 ppb ethanol solution | 0.05 |
| Purified water | balance |
| Total | 100.0 |

(2) Among the formulation for powdered tea (Matcha) pudding use shown in the above Table 4, sucrose, skim milk powder, powdered tea, gelling agent and emulsifying agent were mixed as powders in advance, added to a mixture of whip cream (vegetable fat content: 40%), whole milk condensed whole milk, sweetened, and water, and then dissolved by stirring and heating at 80° C. for 10 minutes. Subsequently, the remaining materials were mixed therewith, and the mixture was adjusted to a total amount of 100 parts with water, homogenized at 14700 kPa, filled in a container and then solidified with cooling to produce a powdered tea pudding. The powdered tea pudding obtained thereby was a powdered tea pudding having an odor which has a deep tea leaf-like image and accompanies a ripen feeling.

Inventive Example 11

<Production of Grapefruit Flavor Composition>

A grapefruit flavor was produced by the formulation shown below, and an extremely small amount of the (1S)-8-mercaptomenthone synthesized in Synthesis Example 4, wherein the mixing ratio of S-form/R-form for the configuration at the 4-position was 75:25, was added thereto. Sensory comparison evaluation of this product and a product to which the compound was not added (Comparative Example 5) was carried out by a panel of 7 specialists.

As a result, all members of the panel judged that a freshness having natural deepness, which was not present in the product of Comparative Example 5, was added to the product of Inventive Example 11 produced by adding the compound.

TABLE 5

| Components | Inventive Example 11 | Comparative Example 5 |
|---|---|---|
| Grapefruit essence | 95.0 | 95.0 |
| Ethyl butanoate | 0.1 | 0.1 |
| Ethyl 2-methylbutanoate | 0.02 | 0.02 |
| Octanal | 0.01 | 0.01 |
| Nootkatone | 0.05 | 0.05 |
| (1S)-8-Mercaptomenthone | 0.000001 | — |
| Ethanol | balance | balance |
| Total | 100.0 | 100.0 |

Inventive Example 12

<Production of Fragrance Composition for Shampoo Use>

TABLE 6

| <Formulation Example 1> | |
|---|---|
| Components | Part(s) |
| Benzyl salicylate | 55 |
| 1-Citronellol | 10 |
| Ethyl acetoacetate | 5 |
| Galaxolide 50 BB* (mfd. by IFF) | 390 |
| Geraniol | 10 |
| Hedione (mfd. by Firmenich) | 120 |
| Heliobouquet (mfd. by Takasago International Corporation) | 8 |
| Cis-3-hexenol 10% DPG** solution | 10 |

TABLE 6-continued

<Formulation Example 1>

| Components | Part(s) |
|---|---|
| Cis-3-hexenyl acetate 10% DPG solution | 5 |
| Hexyl cinnamic aldehyde | 50 |
| β-Ionone | 17 |
| Kovanol (mfd. by Takasago International Corporation) | 40 |
| Lemon oil | 40 |
| Linalool | 45 |
| Linalyl acetate | 45 |
| Nerolidol | 55 |
| Phenylethyl alcohol | 30 |
| Phenylethyl cinnamate | 5 |
| Santalex T (mfd. by Takasago International Corporation) | 35 |
| Triplal 10% DPG solution (mfd. by IFF) | 5 |
| Maltol 1% DPG solution | 15 |
| (1S)-8-Mercaptomenthone 10 ppm DPG solution | 5 |
| Total | 1000 |

*Benzyl benzoate
**Dipropylene glycol

Comparative Example 6

An fragrance composition for shampoo use was prepared by the same formulation of Inventive Example 12, except that dipropylene glycol was used instead of the (1S)-8-mercaptomenthone 10 ppm DPG solution in the same formulation of Inventive Example 12.

Application Example 1

<Production of Shampoo>

Using the fragrance compositions for shampoo use prepared in Inventive Example 12 and Comparative Example 6, the following components were stirred with heating at 80° C. until they became uniform and then cooled to 35° C. to prepare shampoos.

TABLE 7

<Shampoo composition (%)>

| | |
|---|---|
| Sodium lauryl sulfate | 40.00 |
| N-Coconut oil fatty acid acyl-N-carboxymethoxyethyl-N-carboxymethyl ethylenediamine disodium | 10.00 |
| Coconut oil fatty acid diethanolamide (2) | 2.00 |
| Butylene glycol | 2.00 |
| Citric acid | 0.35 |
| Sodium chloride | 0.10 |
| Methyl paraben | 0.20 |
| Propyl paraben | 0.10 |
| Tetrasodium edetate | 0.10 |
| Fragrance composition of Inventive Example 12 or Comparative Example 6 | 0.50 |
| Purified water | balance |
| Total | 100.00 |

Evaluation Results of Shampoos in which the Fragrance Compositions of Inventive Example 12 and Comparative Example 6 are Used As a result of comparative evaluation of the shampoos in which the fragrance compositions of Inventive Example 12 and Comparative Example 6 are used, all members of the panel judged that a fresh and natural feeling having excellent diffusion ability, which was not present in the shampoo using the composition based on the formulation of Comparative Example 6, was added to the shampoo using the fragrance composition prepared based on the (1S)-8-mercaptomenthone-containing formulation of Inventive Example 12.

Inventive Example 13, Comparative Example 7

<Production of Fragrance Composition for Body Shampoo Use>

As shown in the following Formulation Example 2, the fragrance composition for body shampoo use of Inventive Example 13 was prepared using a 10 ppm DPG (dipropylene glycol) solution of (1S)-8-mercaptomenthone wherein the mixing ratio of S-form/R-form for the configuration at the 4-position was 75:25. Also, the fragrance composition for body shampoo use of Comparative Example 7 was prepared based on the same formulation of Inventive Example 13, except that dipropylene glycol was used instead of the 10 ppm DPG solution of (1S)-8-mercaptomenthone.

TABLE 8

<Formulation Example 2>

| Components | Part(s) |
|---|---|
| Lemon oil | 100 |
| Lime oil | 180 |
| Geranyl nitrile | 10 |
| Aldehyde C-8 10% DPG solution | 25 |
| Aldehyde C-10 10% DPG solution | 35 |
| Ethyl decanoate | 12 |
| Triplal (mfd. by IFF) | 3 |
| Isocyclocitral 10% DPG solution | 25 |
| Styralyl acetate | 20 |
| α-Terpineol | 30 |
| Linalool | 70 |
| Linalyl acetate | 50 |
| Geraniol | 60 |
| Geranyl acetate | 5 |
| Lilial (mfd. by Givaudan) | 80 |
| Hexyl cinnamic aldehyde | 120 |
| Myrac aldehyde (mfd. by IFF) | 15 |
| Cis-3-hexenyl salicylate | 15 |
| β-Ionone | 25 |
| Heliotropine | 5 |
| Tonalid (mfd. by PFW) | 30 |
| (1S)-8-mercaptomenthone 10 ppm DPG solution | 5 |
| Total | 1000 |

Application Example 2

<Production of Body Shampoo>

Using the fragrance compositions of Inventive Example 13 and Comparative Example 7, body shampoo of the following composition was prepared.

TABLE 9

<Body shampoo composition (%)>

| | |
|---|---|
| Dibutylhydroxytoluene | 0.05 |
| Methyl paraben | 0.10 |
| Propyl paraben | 0.10 |
| Tetrasodium edetate | 0.10 |
| Potassium chloride | 0.20 |
| Glycerol | 5.00 |
| Coconut oil fatty acid diethanolamide (2) | 3.00 |
| Polyoxyethylene lauryl ether sodium acetate (3 E.O.) (30%) | 10.00 |
| Coconut oil fatty acid amide propyl betaine liquid (34%) | 25.00 |
| Potassium myristate (40%) | 25.00 |

TABLE 9-continued

<Body shampoo composition (%)>

| | |
|---|---|
| Fragrance composition of Inventive Example 13 or Comparative Example 7 | 0.50 |
| Purified water | balance |
| Total | 100.00 |

<Evaluation Results of Body Shampoos in which the Fragrance Compositions of Inventive Example 13 and Comparative Example 7 are Used>

As a result of evaluating the body shampoos produced using the fragrance compositions of Inventive Example 13 and Comparative Example 7, all members of the panel judged that a citrus feeling with improved freshness, which was not present in the body shampoo using the composition based on the formulation of Comparative Example 7, was added to the body shampoo using the fragrance composition prepared based on the (1S)-8-mercaptomenthone-containing formulation of Inventive Example 13.

Inventive Example 14

<Production of Fragrance Composition for Perfume Use>

TABLE 10

<Formulation Example 3>

| Components | Part(s) |
|---|---|
| α-Pinene | 8 |
| Aldehyde C-16 | 1 |
| Allylamyl glycolate | 1 |
| Ambrettolide (mfd. by IFF) | 8 |
| Bergamot oil | 15 |
| Carbitol | 100 |
| Cardamon oil | 3 |
| 1-Citronellol | 30 |
| β-Damascone | 2 |
| Dimethyloctanol 10% DPG solution | 4 |
| Dipropylene glycol | 29 |
| Dynascone 10% DPG solution | 5 |
| Ethyl acetate 10% DPG solution | 4 |
| Ethyl acetoacetate | 15 |
| Galbanum oil 10% DPG solution | 10 |
| Hedione (mfd. by Firmenich) | 195 |
| Heliobouquet (mfd. by Takasago International Corporation) | 10 |
| Cis-3-hexenol | 2 |
| Cis-3-hexenol 10% DPG solution | 3 |
| β-Ionone | 10 |
| Jasmine absolute | 3 |
| Lime oil 10% DPG solution | 5 |
| Linalyl acetate | 40 |
| 8-Mercaptomenthone 10% DPG solution | 8 |
| Musk T (mfd. by Takasago International Corporation) | 200 |
| Nerolidol | 46 |
| Phenylethyl alcohol | 17 |
| β-Pinene | 117 |
| Rhubofix (mfd. by Firmenich) | 12 |
| Rose absolute | 3 |
| Rose oil 10% DPG solution | 5 |
| 1-Rose oxide 10% DPG solution | 15 |
| Santalex T (mfd. by Takasago International Corporation) | 40 |
| Triplal (mfd. by IFF) | 14 |
| Veloutone (mfd. by Firmenich) | 12 |
| Maltol | 5 |
| (1S)-8-Mercaptomenthone 10 ppm DPG solution | 5 |
| Total | 1000 |

Comparative Example 8

A fragrance composition for perfume use was prepared based on the same formulation of Inventive Example 14, except that dipropylene glycol (DPG) was used instead of the 10 ppm DPG solution of (1S)-8-mercaptomenthone in the formulation of Inventive Example 14.

Application Example 3

<Production of Facial Cream>

Using the fragrance compositions for perfume use prepared in Inventive Example 14 and Comparative Example 7, facial creams were prepared.

TABLE 11

<Facial cream composition (%)>

| | |
|---|---|
| Stearyl alcohol | 6.0 |
| Stearic acid | 2.0 |
| Hydrogenated lanolin | 4.0 |
| Squalane | 9.0 |
| Octyl decanol | 10.0 |
| Glycerol | 6.0 |
| Polyethylene glycol 1500 | 4.0 |
| Polyoxyethylene (25) cetyl ether | 3.0 |
| Glycerol monostearate | 2.0 |
| Methyl paraben | proper quantity |
| Ethyl paraben | proper quantity |
| Fragrance composition of Inventive Example 14 or Comparative Example 8 | 0.1 |
| Purified water | balance |
| Total | 100.0 |

<Evaluation Results of Facial Creams in which the Fragrance Compositions of Inventive Example 14 and Comparative Example 8 are Used>

All members of the panel judged that a natural feeling having excellent diffusion ability, which was not present in the facial cream using the fragrance composition of Comparative Example 8, was added to the facial cream using the fragrance composition of Inventive Example 14.

Inventive Example 15, Comparative Example 9

<Tropical Fruit Aroma Composition>

TABLE 12

<Formulation of Tropical fruit flavor composition (%)>

| | |
|---|---|
| Ethyl acetate | 3.00 |
| Ethyl butyrate | 1.50 |
| Hexyl alcohol | 0.15 |
| Hexyl acetate | 0.06 |
| Hexyl butyrate | 0.15 |
| Hexyl hexanoate | 0.25 |
| Cis-3-hexenol | 0.10 |
| Cis-3-hexenyl acetate | 0.05 |
| Cis-3-hexenyl hexanoate | 0.025 |
| Linalool | 0.05 |
| Beta ionone | 0.005 |
| Hexanoic acid | 0.005 |
| 2-Methyl-4-propyl-1,3-oxathiane | 0.01 |
| Furaneol | 0.05 |
| Ethyl alcohol | 54.579 |
| Water | 40.0 |
| Total | 100.0 |

When a product of Inventive Example 15 prepared by adding 0.001% of the 75:25 (1S)-8-mercaptomenthone of Synthesis Example 4 to the tropical fruit flavor composition of the aforementioned formulation was compared with another product prepared by adding 0.001% of the 75:25 (1R)-8-mercaptomenthone of Synthesis Example 7 to the tropical fruit flavor composition of the aforementioned formulation, all members of the panel judged that diffusivity of the characteristic top note of fresh passion fruit was improved and natural sweetness and sourness were emphasized in the passion fruit flavor composition of Inventive Example 15 prepared by adding the compound of Synthesis Example 4.

On the other hand, all members of the panel judged that the product of Comparative Example 9 prepared by using the 75:25 (1R)-mercaptomenthone of Synthesis Example 7 was poor in the diffusivity of flavor, lacked in a natural feeling, was oily, became a dark tone in general and thus resulted in a downcast feeling.

While the invention has been described in detail and with reference to specific embodiments thereof, it will be apparent to one skilled in the art that various changes and modifications can be made therein without departing from the scope thereof.

This application is based on Japanese patent application No. 2005-009811 filed Jan. 18, 2005, the entire contents thereof being hereby incorporated by reference.

What is claimed is:

1. A method for enhancing fruit odor in a flavor or fragrance composition, which comprises adding thereto an optically active (1 S)-8-mercaptomenthone having an S-form/R-form mixing ratio for the configuration at the 4-position of from 75:25 to 95:5 by weight, a chemical purity of 90% or more and an optical purity of 90% e.e. or more.

2. The method according to claim 1, wherein the flavor or fragrance composition is selected from the group consisting of synthetic aroma chemicals, natural essential oils, synthetic essential oils, citrus fruit oils and animal aroma chemicals.

3. The method according to claim 1 or 2, which is a flavor composition.

4. The method according to claim 3, which comprises adding thereto the optically active (1S)-8-mercaptomenthone in an amount of from $10^{-5}$ to $10^3$ ppb by weight based on the total weight of the composition.

5. The method according to claim 1 or 2, which is a fragrance composition.

6. The method according to claim 5, which comprises adding thereto the optically active (1 S)-8-mercaptomenthone in an amount of from $10^{-1}$ to $10^6$ ppb by weight based on the total weight of the composition.

* * * * *

UNITED STATES PATENT AND TRADEMARK OFFICE
CERTIFICATE OF CORRECTION

PATENT NO. : 8,575,086 B2
APPLICATION NO. : 11/333367
DATED : November 5, 2013
INVENTOR(S) : Makoto Emura et al.

It is certified that error appears in the above-identified patent and that said Letters Patent is hereby corrected as shown below:

In the Specifications

COLUMN 1:

Line 23, "highly-tasting" should read --good-tasting and--;
Line 24, "uprush" should read --popularity--;
Line 61, "the" should be deleted;
Line 63, "+220," should read --+22°,--; and
Line 66, "($\alpha_D^{20}$ 124.2°)" should read --($\alpha_D^{20}$ = 124.2°)--.

COLUMN 2:

Line 8, "highly-" should read --good- --;
Line 11, "an" should read --a--; and
Line 32, "followings." should read --following:--.

COLUMN 3:

Line 57, "mixture" should read --mixtures--.

COLUMN 5:

Line 49, "highly-tasting" should read --good-tasting--; and
Line 57, "3-form/R-form" should read --S-form/R-form--.

COLUMN 6:

Line 6, "is" should read --are--;
Line 14, "1969'" should read --1969--;

Signed and Sealed this
Fourth Day of February, 2014

Michelle K. Lee
*Deputy Director of the United States Patent and Trademark Office*

Line 28, "high tasting," should read --good taste,--; and
Line 39, "high-tasting" should read --good-tasting--.

COLUMN 7:

Line 5, "Perfum," should read --Parfum,--;
Line 8, "make" should read --makeup--;
Line 40, "breaching" should read --bleaching--;
Line 45, "toilette" should read --toilet--; and
Line 57, "mouse" should read --mouth--.

COLUMN 8:

Line 7, "matters;" should read --matter;--;
Line 11, "matters" should read --matter--; and
Line 22, "cyclodextrin" should read --cyclodextrin.--.

COLUMN 12:

Line 27, "an" should be deleted;
Table 1, "is lack" should read --lacks--,
    "accompanies" should read --is accompanied by--, and
    "somewhat miscellaneous" should read --some miscellaneous--;
Line 58, "reminded the" should read --resembled--; and
Line 59, "highly-tasting" should read --good taste with a--.

COLUMN 13:

Line 6, "to a" should read --of--;
Line 34, "to a" should read --of--; and
Line 35, "but" should read --but was--.

COLUMN 14:

Line 33, "ripen" should read --ripe--;
Line 40, "an" should read --a--; and
Line 60, "ripen" should read --ripe--.

COLUMN 15:

Line 60, "whip" should read --whipped--.

CERTIFICATE OF CORRECTION (continued)
U.S. Pat. No. 8,575,086 B2

COLUMN 16:

Line 13, "whip" should read --whipped--; and
Line 21, "ripen" should read --ripe--.

COLUMN 17:

Line 25, "An" should read --A--.

COLUMN 21:

Line 10, "in" (second occurrence) should be deleted.

In the Claims

COLUMN 22:

Line 18, Claim 6, "(1 S)-8-mercaptomen-" should read --(1S)-8-mercaptomen- --.